United States Patent [19]

Vincenti et al.

[11] Patent Number: 4,767,875
[45] Date of Patent: Aug. 30, 1988

[54] PROCESS FOR SYNTHESIS OF ALUMINUM COORDINATIONS COMPOUNDS

[75] Inventors: Paul J. Vincenti, Parsippany, N.J.; James D. Warren, Pearl River, N.Y.

[73] Assignee: American Cyanamid Company, Stamford, Conn.

[21] Appl. No.: 762,084

[22] Filed: Sep. 9, 1985

[51] Int. Cl.$^4$ ............................................. C07F 5/06
[52] U.S. Cl. ............................................. 556/175
[58] Field of Search ................................. 556/175

[56] References Cited

U.S. PATENT DOCUMENTS

| | | | |
|---|---|---|---|
| 2,801,190 | 7/1957 | Arthner et al. | 556/182 X |
| 2,823,169 | 2/1958 | Brown et al. | 556/182 |
| 3,256,188 | 6/1966 | Papayannopoulos | 556/182 X |
| 3,420,932 | 1/1969 | Jones et al. | 556/182 X |
| 3,444,226 | 5/1969 | Schmank et al. | 556/175 |
| 3,444,292 | 5/1969 | Beekman et al. | 556/175 X |
| 3,472,929 | 10/1969 | Jones et al. | 556/182 X |
| 3,792,070 | 2/1974 | Jones et al. | 556/175 |
| 3,819,671 | 6/1974 | Bouillon et al. | 556/175 |
| 3,956,352 | 5/1976 | Bouillon et al. | 556/175 |

Primary Examiner—Paul F. Shaver
Attorney, Agent, or Firm—C. J. Flickey

[57] ABSTRACT

A method for producing heterocyclic aluminum compounds of the formula:

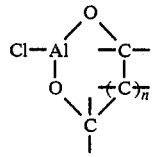

where n is 0 to 1, by reacting aluminum chloride with an aliphatic polyhydric alcohol having from 2 to 6 carbon atoms and having hydrogen, hydroxy, or low alkyl groups on carbon atoms which are spaced apart by no more than one intervening carbon atom, which is useful as an anti-perspirant.

5 Claims, No Drawings

PROCESS FOR SYNTHESIS OF ALUMINUM COORDINATIONS COMPOUNDS

The present invention relates to heterocyclic organic aluminum compounds and to methods for their preparation. The compounds of the present invention are particularly useful for anti-perspirants.

The requirements for anti-perspirant compositions are quite rigorous. The anti-perspirant compositions must form homogenous systems in both fluid and solid form. They must be stable for reasonable storage periods. They should contain only trace amounts of iron, since this metal inactivates compounds such as "hexachlorophene" and also catalyzes degradation of some organic perfume materials. The anti-perspirant compositions should have a low acidity pH range on the order of 3.5 to 4.5 when mixed with water. They must be sufficiently soluble to be effective and they must be safe to use daily on the skin. Most important, they must be effective in inhbiting the flow of perspiration on the axillae.

Aluminum chloride hexahydrate has been used as an anti-perspirant composition for a long period of time. Although it is compatible with anhydrous ethanol, and compatible with propellants, and is an effective anhydrotic, it is too acid to use daily, and has adversely affected the tensile strength of fabrics. Less acid materials such as aluminum phenolsulphonate have been used as anti-perspirant composition, but the anti-perspirant activity of these materials is quite low. The patent literature also includes a disclosure of aluminum chlorhydroxide alcoholate having 0.25 to 1 hydroxyl for each aluminum atom in anti-perspirant compositions (U.S. Pat. No. 2,823,169). These materials, however, are rather unstable and they contain more than a trace amount of iron, usually including on the order of 40 to 80 parts per million of iron. U.S. Pat. No. 2,872,379 discloses a series of alkoxy aluminum chlorides as antiperspirants, but these compounds are limited in usefulness because of their very low solubility in anhydrous alcohol. Such a group of compounds are described in U.S. Pat. No. 3,444,292, and are cyclic organo-aluminum compounds.

An object of the present invention is to provide an improved process for preparing organo-aluminum compounds useful as antiperspirants. This and other objects will become apparent as the description of the invention proceeds.

The compounds produced in the process of the present invention have the following generic formula:

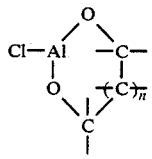

where n is an integer from 0 to 1.

As indicated in the above structural formula, the heterocyclic compounds of the present invention include a ring structure which may number from 5 to 6 atoms in the ring. The linkage:

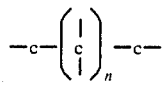

forming part of the above identified structural formula is preferably a residue of an aliphatic polyhydric alcohol having from 2 to 6 carbon atoms per molecule and having hydroxyl atoms on carbon atoms which are spaced apart by no more than one intervening carbon atom.

The valance bonds shown in the above structural formula should be attached to groups which do not have an adverse effect upon the solubility or the acidity of the resulting compound, and should preferably be either hydrogen atoms, hydroxyl groups, or low alkyl chains (up to 3 carbon atoms).

The above described compounds are produced, in the process of the present invention, by reacting aluminum chloride with an aliphatic polyhydric alcohol having from 2 to 6 carbon atoms and having carboxyl groups of carbon atoms which are spaced apart by no more than one intervening carbon atom.

This basic reaction was described and claimed in copending, commonly assigned application Ser. No. (Case 29,357), filed Aug. 2, 1985. In the copending application, the reaction was conducted in the presence of diethyl ether for about five hours, at room temperature, the product was washed with diethyl ethers, dried under vacuum, at room temperature suspended in diethyl ether, filtered, rinsed with diethyl ether and again dried under vacuum at room temperature. It was found that the product contained residual hydrogen chloride and diethyl ether and this made the product less satisfactory when applied to the skin for use in an antiperspirant composition.

The present process is described generally as follows:

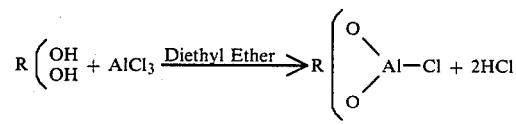

The reaction as stated provides the diol complexes in good yield, but is complicated by the moisture sensitivity of the product. Even under strict conditions (freshly distilled ether, anhydrous AlCl$_3$, 99+% propylene glycol, all under a nitrogen atmospher) the water content of the product was measured at 10%. With this amount of water present, the following hydrolysis most likely takes place:

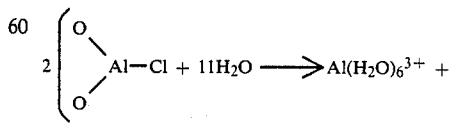

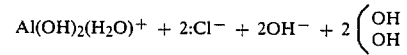

followed by a secondary hydrolysis of the hex-aaquoaluminum ion. The final result of that hydrolysis is intimately connected to the pH of the system:

$$Al(H_2O)_6^3 + OH^- \rightarrow Al(OH)_x(H_2O)_y$$

Therefore, a proper representation of the product is a mixture of the original diol complex, water, and hydrolysis products. Since this process provides material which is of commercial interest in its present form, more costly and complicated purification methods would not be feasible in our process. Also, constraints that we could practice in a laboratory environment would be unsuitable for production level of this material. A final purity of 80–85% is probably a good estimate when moisture and hydrolysis products are taken into account.

Suitable solvents are organic solvents having a dielectric constant from about 2 to 20 and boiling at a temperature of not greater than about 100° C. such as diethyl ether and others described subsequently in Table I.

It has been found that if the final rinses and vacuum drying are eliminated, and the product is heated at elevated temperature, e.g. 90° C., for about 48 hours, a high yield of product is obtained, over 90% yield. The product is also free of residual hydrogen chloride and diethyl ether. Thus, the product is useful in compositions for application to the skin as an antiperspirant, and is highly efficacious for this purpose.

It may be desirable when use a more volatile solvent, e.g. diethyl ether, to subject the product to vacuum drying to remove some of the solvent. But this is not necessary to the process.

It was highly surprising that the final heating step could be utilized without detriment and with the beneficial results obtained.

The product of the invention is not normally ethanol soluble, but this is not a limitation since it is soluble in aqueous ethanol solutions.

The present process produces more economically and efficiently a complex which has shown marked utility in the inhibition of perspiration versus the untreated axillary area, namely a 45.4% reduction in perspiration. With respect to the previously claimed 2-Chloro-4-diethyl-1,2,3-Dioxalumolane (U.S. Pat. Nos. 3,444,226 and 3,444,292), the preparation of the present application results in a non-solvated species as well as yields in excess of 90%. The reaction utilizes readily available materials and accomplishes the reaction at room temperature rather than in refluxing isopropanol at an elevated temperature of 82° C. to 83° C.

The following specific examples illustrate preparation of the organo-aluminum complexes by the process of the present invention, and the efficaciousness of these compounds as antiperspirant compounds.

The scale of these reactions range from 2–1800 g depending on the diol used with 1,2-propanediol being the most heavily investigated. The reaction seems to be quite general with respect to diol, however, if the hydroxyl groups are separated by more than 3–4 carbon atoms, competitive reactions may result. Chelation of the two ends onto the aluminum center may be concurrent with monodentate attachment on either end of the diol. Also, other functional groups (eg. ester or ether groups) may also interact with the metal center. Finally, solvent choices seems to preclude straight chain hydrocarbons (solubility/decomposition) and/or low molecular weight alcohols (may form complexes with the aluminum reagent).

EXAMPLE I

Anhydrous aluminum chloride (75 g; 0.56 mole) was combined with 500 ml diethyl ether in a 2 liter flask which had been cooled in an ice/acetone bath. The order of addition is more important as the scale is increased. At large scale, the diethyl ether should be cooled prior to addition of the aluminum chloride to prevent decomposition of the metal halide. Such decomposition is not evident when small scale (75 g $AlCl_3$ or less) reactions are run. Upon mechanical stirring, the metal halide completely dissolved upon addition. Dropwise addition of 1,2-propanediol (41.3 ml; 0.56 mole) resulted in the precipitation of a white solid. After stirring for 4.5 hours under nitrogen at room temperature, the white solid was filtered and washed with 400 ml diethyl ether. The product was dried under vacuum at room temperature for 15 hours. After suspending the product in diethyl ether and filtering, another 15 hours of vacuum drying at room temperature was carried out. After this time, the temperature was raised to 90° C. for an additional 48 hours. The white solid (72.2 g; 94% yield calculated in accordance with the molecular formula $C_3H_6OAlCl$) was stored in a desiccator over calcium sulfate.

Elemental analysis of the compound shows that the molecular unit $OCH_2CH(Me)OAlCl$ is present. This is further verified by vapor phase osmometry in 1,2-propanediol which gives a molecular weight of 142 (136.5 calculated). Hydrolysis upon dissolution in water results in resonances for the free 1,2-propanediol ligand in the $^1H$ and $^{13}C$ NMR spectra.

EXAMPLE II

The reaction of the present invention was carried out with a number of diols and at varying temperature, as shown in table I.

Table I contains information on 9 diol ligands, 10 solvent variations, and reaction temperatures spanning a range of $-10°$–$111°$ C. Data on reactions that did not provide the diol complex is also included. The molar ratio of aluminum and chlorine is given with the ideal ratio being equal to 1.0.

EXAMPLE III

In this Example, a number of diols were used on varying quantitative reaction scales. The results, yields and product analysis are shown in table II.

EXAMPLE IV

Antiperspirant Efficacy of Propylene Glycol-Aluminum Chloride Complex vs. Aluminum Zirconium Glycine (CEL #'s 83-31 and 83-35; A/P Screening Tests)

Antiperspirant (A/P) screening test CEL 83-31 was conducted to construct a dose-response curve by evaluating A/P efficacy of various amounts of 12.6% PG-AlCl (propylene glycol-aluminum chloride, CPRD #13857); 0.5 ml Al:Zr-Gly (24%; aluminum zirconium glycine, CPRD #13384) was used as a benchmark for efficacy. Although the lowest amount of PG-AlCl (41 mg active) did not yield a sweat reduction that significantly exceeded 20%, all other amounts ($\geq 68$ mg active) did so, and were equieffective with respect to each other and the benchmark amount of Al:Zr-Gly. CEL 83-35 was conducted to supplement the data points where the two test compounds were administered on an equivalent metal basis (ca. 35 mg/application). In that investigation, Al:Zr-Gly was 26% more effective than PG-AlCl ($p<0.05$), but when the results of both studies were combined (N=51), the two compounds did not differ at the 90% level of confidence, with Al:Zr-Gly directionally more effective.

TABLE I

| TEMPERATURE | LIGAND | SOLVENT | ANALYSIS |
|---|---|---|---|
| $-10°-25°$ C. | 1,2-propanediol | $Et_2O$ | $Cl/Al = 1.0$ |
| $-10°-40°$ C. | (CL 282,006) | $CH_2Cl_2$ | $Cl/Al = 1.0$ |
| $-18°-25°$ C. | | THF | $Cl/Al = 1.0$ |
| $25°-82°$ C. | | iPrOH | $Cl/Al = 1.1$ |
| $25°$ C. | | $C_7H_{16}$ | NR |
| $0°-25°$ C. | | $C_4H_9Br$ | NR |
| $0°-25°$ C. | | $MeOCH_2CH_2OMe$ | mixture of products |
| $0°-78°$ C. | | EtOH | mixture of products |
| $-10°-25°$ C. | 1,3-propanediol | $Et_2O$ | $Al/Cl = 1.2$ |
| $-10°-34°$ C. | 1,3-butanediol | $Et_2O$ | $Cl/Al = 1.1$ |
| $-10°-25°$ C. | 1,4-butanediol | $Et_2O$ | $Cl/Al = 1.0$ |
| $25°$ C. | (CL 282,012) | $C_6H_{14}$ | NR |
| $-10°-34°$ C. | 2,3-butanediol | $Et_2O$ | $Cl/Al = 1.0$ |
| $25°-82°$ C. | | iPrOH | $Cl/Al = 1.2$ |
| $25°-69°$ C. | | $C_6H_{14}$ | NR |
| $0°-82°$ C. | glycerol | iPrOH | $Al/Cl = 1.1$ |
| $-10°-25°$ C. | glycerol-1-acetate | $Et_2O$ | mixture of products |
| $-10°-25°$ C. | hexylene glycol | $Et_2O$ | mixture of products |
| $25°-111°$ C. | decylene glycol | toluene | NR |
| $25°-34°$ C. | | $Et_2O$ | NR |

NR = no reaction/decomposition

TABLE II

| LIGAND/SOLVENT | SCALE | COMPLEX YIELD | Average Analysis COMPLEX | $H_2O$ | IMPURITY |
|---|---|---|---|---|---|
| $PG/Et_2O$ | 1800 g | 89% | 92% | 4.6% | 3.4% |
| $PG/Et_2O$ | 800 g | 92% | 92% | 2.8% | 5.2% |
| $PG/CH_2Cl_2$ | 10 g | 47% | 80% | 15% | 5% |
| PG/THF | 26 g | 55% | 79% | 7.3% | 13.7% |
| PG/iPrOH | 5 g | — | 80% | 12% | 8% |
| 1,3-propanediol/$Et_2O$ | 5 g | 66% | 82% | 8% | 10% |
| 1,3-butanediol/$Et_2O$ | 10 g | 31% | [68%] | [29%] | 3% |
| 1,4-butanediol/$Et_2O$ | 6 g | 76% | 91% | 5.5% | 3.5% |
| 2,3-butanediol/$Et_2O$ | 10 g | 42% | 80% | 10% | 10% |
| 2,3-butanediol/iPrOH | 27 g | 18% | 82% | 9% | 9% |
| glycerol/iPrOH | 18 g | 81% | 81% | 2% | 17% |
| | | | 84%* | 7.6%* | 8.4%* |

*w/o 1,3-butanediol product
impurity = excess diol and/or dydrolysis product

METHODOLOGY

Respondents. One hundred three women participated in CEL 83-31; 51 different subjects took part in CEL 83-85. In both studies, respondents refrained from antiperspirant use for a 17-day period prior to the start of the tests. They were permitted ad libitum use of OLD SPICE ® Aerosol Deodorant during the conditioning period and shaved their axillae no less than three days before the test began.

Products. The treatments evaluated in these studies uses laboratory scale solutions and were applied by syringe. Details are shown in Table III:

TABLE III

| Description | CPRD # | Active and % Conc. | Amount Applied (ml) | Studies Evaluated |
|---|---|---|---|---|
| A/P Solution | 13857 | PG—AlCl 12.6% | 0.324 | 83-31 |
| A/P Solution | 13857 | PG—AlCl 12.6% | 0.54 | 83-31 |
| A/P Solution | 13857 | PG—AlCl 12.6% | 0.90 | 83-31 |
| A/P Solution | 13857 | PG—AlCl 12.6% | 1.50 | Both |
| A/P Solution | 13857 | PG—AlCl 12.6% | 2.50 | 83-31 |

TABLE III-continued

| Description | CPRD # | Active and % Conc. | Amount Applied (ml) | Studies Evaluated |
|---|---|---|---|---|
| A/P Solution | 13384 | Al:Zr—Gly 24.0% | 0.50 | Both |
| Untreated | — | — | — | Both |

The various amounts of CPRD 13857 applied in CEL 83-31 are equally spaced on a log scale; successive amounts increase by a factor of 1.67.

Procedure. On Days 1, 2, and 3 of 83-31, respondents washed their axillae with 3% soap under supervision; unilateral treatment with one of the five amounts of CPRD 13857 or 0.5 ml CPRD 13384 followed. Each respondent's other axilla was untreated: the left side for half and the right for the remainder. The same axilla of a given subject was treated each day. On Day 4, respondents sat in the CEL hot room for 80 minutes. Sweat output from minutes 41 through 60 and 61 through 80 was measured gravimetrically. The results of these two intervals were averaged.

The procedures were similar for CEL 83-35, but a round-robin design was employed. Respondents received two of the following treatments (one per axilla): 1.50 ml CPRD 13857, 0.50 ml CPRD 13384, or untreated. Thus, two-thirds rather than all of the respondents had an untreated axilla, with the remainder testing the two solutions head-to-head.

RESULTS

Table IV presents mean mg sweat output and percent reduction versus untreated and results of statistical analysis for CEL 83-31:

TABLE IV

Results of CEL 83-31

| Treatment | Amount Applied (ml) | mg PG-AlCl | Mean Sweat Output (mg/20 min.) | N | % Reduction vs. Untreated (95% C.L.) | Significance* |
|---|---|---|---|---|---|---|
| CPRD 13857 (PG—AlCl) | 0.324 | 41 | 274 | 17 | 28.59 (3.05, 47.41) | a |
| CPRD 13857 (PG—AlCl) | 0.54 | 68 | 184 | 18 | 52.04 (35.47, 64.35) | a,b |
| CPRD 13857 (PG—AlCl) | 0.90 | 113 | 135 | 17 | 64.85 (52.28, 74.11) | b |
| CPRD 13857 (PG—AlCl) | 1.50 | 189 | 153 | 17 | 59.98 (45.66, 70.52) | b |
| CPRD 13857 (PG—AlCl) | 2.50 | 315 | 176 | 17 | 54.01 (37.56, 66.12) | b |
| CPRD 13384 (Al:Zr—Gly) | 0.50 | — | 193 | 17 | 49.58 (31.55, 62.87) | a,b |
| Untreated | — | — | 383 | 103 | 0 | c |

*Treatments with the same letter are not significantly different (p > .05)

It can be seen in Table IV above that all treatments produced significant reductions versus untreated and that increasing tha mount of PG AlCl above 0.9 ml (113 mg active) did not result in significantly greater efficacy.

Table V below presents the corresponding data from CEL 83-35:

TABLE V

Results of CEL 83-35

| Treatment | Amount Applied (ml) | Mean Sweat Output (mg/20 min) | N | % Reduction vs. Untreated (95% C.L.) | Significance |
|---|---|---|---|---|---|
| CPRD 13857 (PG—AlCl) | 1.50 | 135 | 34 | 63.31 (50.59, 72.75) | a |
| CPRD 13384 (Al:Zr—Gly) | 0.50 | 100 | 34 | 72.86 (63.45, 79.85) | b |
| Untreated | — | 367 | 34 | 0 | c |

Both treatments produced mean sweat reductions significantly greater than 20% (p<0.05). This direct comparison of the two actives on a "metal per application" basis indicates that the Al:Zr-Gly was more effective than the PG-AlCl, at least at 3.5 mg Al (p<0.05). Examination of the results shown in Tables IV and V revealed that whereas the sweat outputs from PG-AlCl and untreated were consistent in the two experiments, the Al:Zr-Gly was considerably more effective in CEL 83-35. The performance of the Al:Zr-Gly in this experiment is considerably better than its "track record" under comparable conditions in the CEL: a 44.1% reduction in CEL 83-13 and 57.4% in CEL 83-27. Conclusions regarding the comparative efficacy of these compounds at 3.5 mg Al should take this into account.

When the results of 83-31 and 83-35 are pooled, the advantage of Al:Zr-Gly over PG-AlCl is reduced to one of directionality, as shown in Table VI.

TABLE VI

Pooled Results of CEL 83-31 and 83-35

| Treatment | Amounts Applied (ml) | Mean Sweat Output (mg/20 min.) | N | % Reduction vs. Untreated (95% C.L.) |
|---|---|---|---|---|
| CPRD 13857 (PG—AlCl) | 1.50 | 148 | 51 | 58.89 (49.62. 66.46) |
| CPRD 13384 (Al:Zr—Gly) | 0.50 | 125 | 51 | 65.35 (57.52. 71.74) |
| Untreated | — | 360 | 68 | 0 |

Statistical analysis of these combined results indicated that the two treatments do not differ significantly in efficacy at the 0.05 level of significance. It was determined that the compounds do not differ at the 0.10 level of significance, but would differ at 80% confidence (i.e., 0.10<p<0.20).

The conclusion from this Example is that the antiperspirant composition of the present invention is as efficaceous as aluminum—zirconium glycine, the most effective antiperspirant presently known.

What is claimed is:

1. A method for producing a chemical compound having the formula:

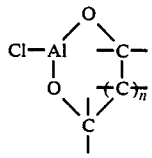

where n is an integer from 0 to 1, the unsatisfied valences in the above formula being attached to at least one member of the group consisting of hydrogen atoms, hydroxyl groups, and alkyl radicals containing up to 3 carbon atoms and the linkage —C—(C)n—C— is a residue of an aliphatic polyhydric alcohol containing from 3 to 6 carbon atoms per molecule which comprises conducting a reaction between aluminum chloride with an aliphatic polyhydric alcohol having from 2 to 6 carbon atoms and having hydroxyl; groups on carbon atoms which are spaced apart by no more than one intervening carbon atom, and subsequently heating the product of said reaction at elevated temperature.

2. The method of claim 1 wherein said subsequent heating is for a time of 24 to 40 hours, at a temperature not greater than about 120° C.

3. The method of claim 1 wherein said reaction is conducted at substantially room temperature.

4. The method of claim 1 wherein the reaction is conducted in the presence of an organic solvent having a dielectric constant from about 2 to about 20 and a boiling point of not greater than about 100° C.

5. The method of claim 1 wherein said product is vacuum dried before said heating at elevated temperature.

* * * * *